United States Patent [19]

Dorband et al.

[11] Patent Number: 4,606,345
[45] Date of Patent: Aug. 19, 1986

[54] SURGICAL INSTRUMENT FOR APPLYING TWO-PIECE FASTENERS COMPRISING U-SHAPED STAPLES AND FRICTIONALLY HELD RECEIVERS (CASE II)

[75] Inventors: Glen C. Dorband, Somerville; Stephen J. Failla, Chester; John Kula, Budd Lake, all of N.J.

[73] Assignee: Ethicon, Inc., Somerville, N.J.

[21] Appl. No.: 631,118

[22] Filed: Jul. 16, 1984

[51] Int. Cl.⁴ .................... A61B 17/00; A61B 17/12
[52] U.S. Cl. .......................... 128/334 R; 112/169; 227/DIG. 1; 128/334 C
[58] Field of Search ............... 128/334 R, 334 C; 112/169; 227/DIG. 1

[56] References Cited

U.S. PATENT DOCUMENTS

| | | | |
|---|---|---|---|
| 4,448,194 | 5/1984 | DiGiovanni | 128/334 R |
| 4,470,532 | 9/1984 | Froehlich | 128/334 R X |
| 4,508,253 | 4/1985 | Green | 227/19 |

Primary Examiner—Lucille M. Phynes
Attorney, Agent, or Firm—Robert L. Minier

[57] ABSTRACT

A surgical instrument for applying two-piece fasteners to join tissue. The instrument includes a stationary jaw and a movable jaw mounted on a support body. The movable jaw holds the staple portion of the fastener and the stationary jaws include friction means for holding the receiver portion of the fasteners.

3 Claims, 17 Drawing Figures

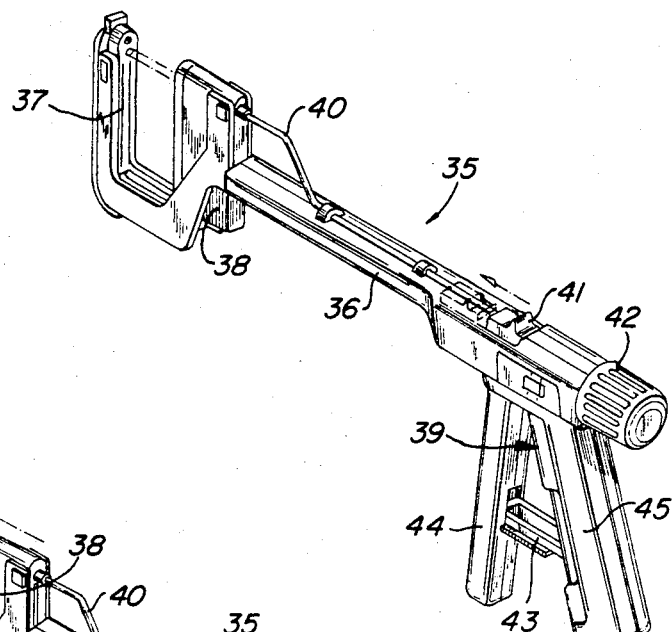
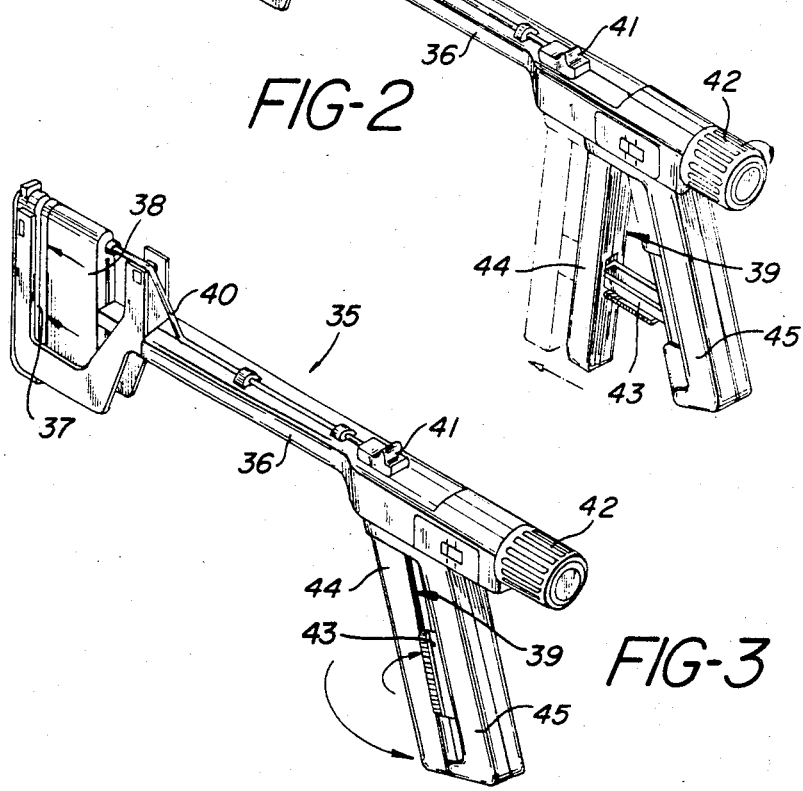

SURGICAL INSTRUMENT FOR APPLYING TWO-PIECE FASTENERS COMPRISING U-SHAPED STAPLES AND FRICTIONALLY HELD RECEIVERS (CASE II)

This invention relates to medical instruments and more particularly to instruments for joining tissue by using two piece fasteners. One part of the fastener is a U-shaped staple and the other part of the fastener is a receiver which interlocks with the legs of the staple to form the fastener.

BACKGROUND OF THE INVENTION

Over the years various surgical instruments for joining tissue have been developed. Most instruments have been developed utilizing metal staples for joining the tissue. The metal staples are relatively rigid, have their legs sharpened to readily penetrate the tissue, and once penetrated may then be crimped into a clinched position to hold the tissue together as is well known in the art. Instruments of this type are more fully disclosed and described in U.S. Pat. Nos. 3,080,564, 3,079,606, 2,891,250, 3,589,589, 4,207,898 and 4,351,466.

Generally, the instruments comprise a movable member or jaw and a stationary member or jaw. The movable jaw usually carries the metal staples and the stationary jaw carries an anvil which clinches or bends the legs of the staple that pass through the tissue. In use, the tissue is placed between the jaws, the jaws brought to the appropriate gap and the staples driven through the tissue and clinched to set the staple. A major problem with these instruments is the use of the metal staple. While metal staples provide desired hemostatsis in the joining of the tissue, they remain in the tissue and can disrupt future diagnostic techniques such as X-ray diagnosis, computer axial tomography, nuclear magnetic resonance, and the like. To eliminate this problem, it has been found desirable to develop instruments which can place non-metallic fasteners. These are fasteners made from biologically absorbable or non-absorbable polymeric materials. Examples of such non-absorbable polymeric materials would be the polyolefins, polyesters, and the like. Examples of the absorbable polymeric materials would be the polymers and copolymers of glycolide, lactide, dioxanone, etc. These polymeric materials do not have the dead-bend morphology of a metal and, hence, they cannot be clinched in the same manner as a metal staple. To use these polymers, the fasteners are designed as two-piece fasteners. This means one piece of the fastener is placed on one side of the tissue to be joined and the second piece of the fastener is placed on the other side of the tissue to be joined. One piece of the fastener is a U-shaped staple which has legs which are caused to penetrate the tissue. On the opposite side of the tissue is the second fastener piece or receiver which is a member used to engage the legs of the staple and interlock therewith once the legs have penetrated the tissue and, hence, join the tissue together.

As can be appreciated this major change in design and configuration of fasteners causes a number of problems. First, the fasteners must be designed to be sufficiently sharp and strong to penetrate the tissue or in certain instances some aiding means must be used with the fastener to assist the fastener in penetrating tissue. Also, the fasteners must be designed to develop an interlocking between the two pieces.

These differences cause various types of forces to be used when joining the tissue together, and these forces are different from the forces required when joining tissue using metallic fasteners. Also, when utlizing the two-piece fasteners, alignment between the two fasteners is extremely critical. As can be appreciated, when applying these two-piece fasteners the instrument must hold both pieces until one piece has penetrated the tissue and the opposite piece is interengaged and locked on to the penetrating portion of the other piece. Once this is accomplished the instrument then releases both pieces preferably simultaneously. It is an object of the present invention to provide an instrument that releasably holds both staples and receivers in a manner to allow their ready placement in tissue to join tissue together. It is a further object of the present invention to provide a suitable instrument which can accept and control the various forces required when placing two-piece non-metallic fasteners. It is also an object of the present invention to provide both staples and fasteners which can be readily aligned and interengaged when used in the instruments of the present invention. Further objects and purposes of the present invention will be readily apparent from the following detailed description.

SUMMARY OF THE PRESENT INVENTION

In accordance with the present invention a surgical instrument for joining tissue is provided. The instrument uses two piece fasteners with the fasteners comprising a substantially U-shaped staple member and a receiver which interengages and interlocks with the legs of said staple. The instrument comprises a pair of oppositely disposed jaws, one of which holds the U-shaped staple members and the other of which holds the receivers for interlocking with the legs of the staples. In use, tissue is placed between the jaws of the instrument with the staple member placed on one side thereof and the receiver placed on the other side thereof. When the instrument is actuated, the legs of the staple are caused to penetrate the tissue to be joined, with the connecting span of the staple lying on one side of the tissue and the receiver lying on the opposite side of the tissue and interlocking with the legs of the staple to join the tissue.

The jaw holding the receivers includes friction means which maintain the receivers in their appropriate position within the jaw. The instrument further includes means for automatically releasing the friction means once the receivers have been engaged and interlock with the legs of the staple. In certain embodiments of the present invention the friction means holds the receiver about the outer periphery thereof. In other embodiments of the present invention, wherein the receivers have openings therein the receivers are frictionally held by members releasably mounted in the openings. In certain embodiments of the present invention, the receivers interengage with the legs of the staple and interlock therewith by virtue of an interference fit. Further embodiments and details of the present invention will become apparent upon reading the ensuing detailed description.

BRIEF DESCRIPTION OF THE DRAWINGS

FIG. 1 is a perspective view of an instrument according to the present invention in its fully opened position;

FIG. 2 is a perspective view of the instrument of FIG. 1 in a partially open position;

FIG. 3 is a perspective view of the instrument of FIG. 1 in its firing position;

DETAILED DESCRIPTION OF THE DRAWINGS

Figure 4:
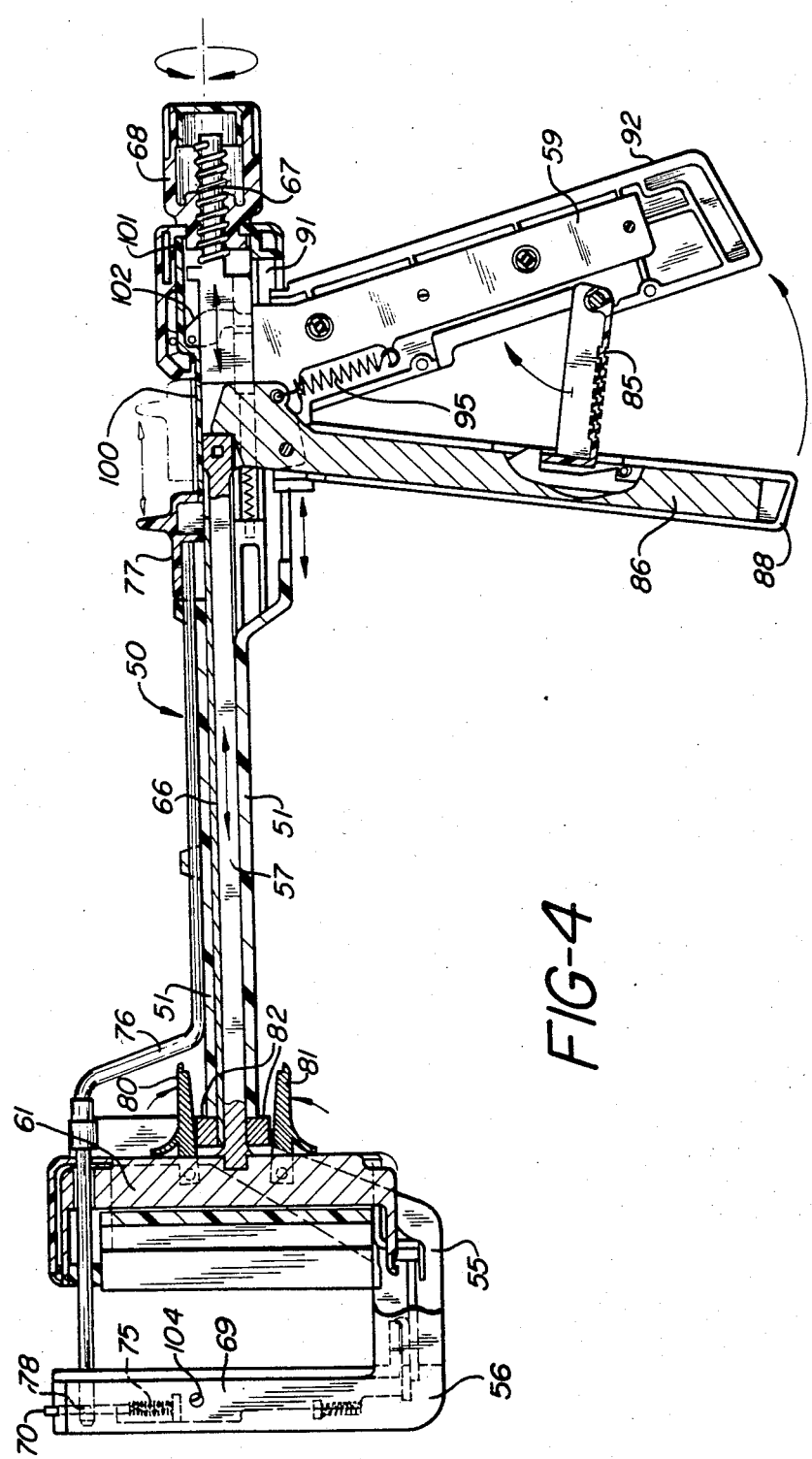
FIG. 4 is a cross-sectional view of another embodiment of a surgical instrument according to the present invention.

Referring to the drawings, in FIGS. 1, 2 and 3 there is depicted a surgical instrument 35 of the present invention useful for joining tissue. The instrument is depicted in three different positions.

In FIG. 1, the instrument is shown in the fully open position. The instrument comprises a support body, 36. A pair of jaws 37 and 38 are positioned at one end of the support body. Mounted at the opposite end of the support body is means 39 for actuating the instrument. In FIG. 1, the jaws of the instrument are in the open position ready to be placed about the tissue to be joined.

In FIG. 2, the jaws have been moved closer to one another to produce an appropriate gap to clamp tissue in position between the jaws so that the tissue is ready to be stitched together.

FIG. 3 shows the instrument after it has been actuated and the tissue has been joined by the instrument.

One of the jaws 37 is stationarily mounted at one end of the support body 36. This jaw carries a plurality of receivers of the two-part fastening members used with the instruments of the present invention. The opposite jaw 38, carries the U-shaped fastening members, and is movably mounted on the support body. The tissue to be joined is placed between the two jaws and the movable jaw positioned with respect to the stationary jaw at an appropriate gap. Once the tissue is placed between the jaws, the locking arm 40 is moved forwardly by the pusher 41 to insure that the tissue is held between the jaws. Once the arm is set and engaged by the stationary jaw, the knob 42 at the opposite end of the support body is turned to move the movable jaw towards the stationary jaw and set the appropriate gap between the jaws. Once the gap has been appropriately set, the trigger locking lever 43 may be disengaged and the movable portion 44 of the actuating trigger means moved towards the stationary portion 45 of the trigger means to cause an appropriate pusher to drive the staples forward causing the legs of the staples to penetrate the tissue between the jaws and the legs of the staples to enter the appropriate receivers held in the stationary jaw. Once this is accomplished the knob 42 may be turned in the opposite direction to open the jaws, the locking lever pushed back and the joined tissue separated from the jaws of the instrument.

Figure 5:
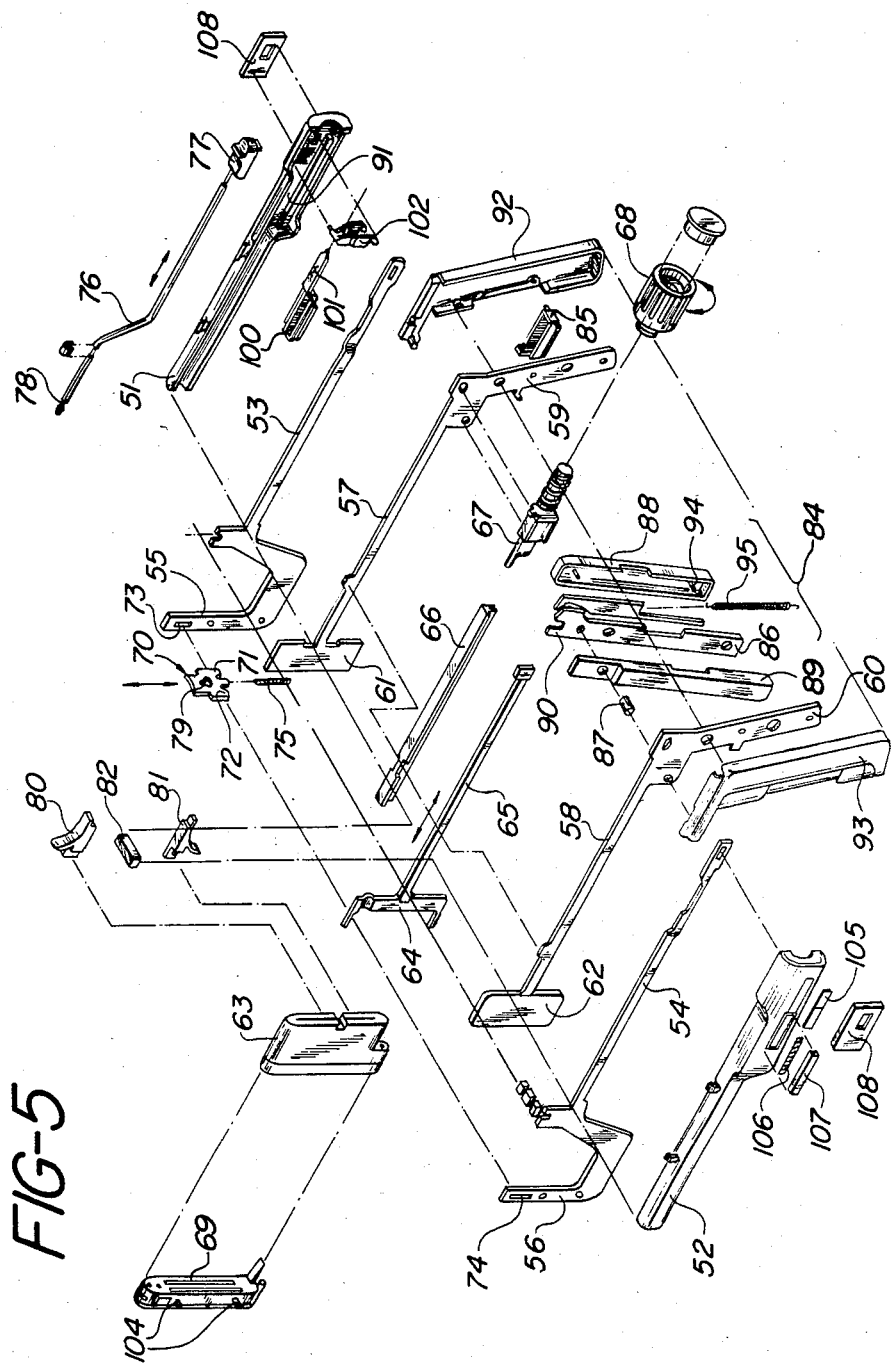
FIG. 5 is an exploded perspective view of the surgical instrument of FIG. 4.

FIG. 4 is a cross-sectional view of one embodiment of a surgical instrument according to the present invention and FIG. 5 is an exploded perspective view showing the different parts of the surgical instrument shown in FIG. 4. The body 50 of the instrument comprises a pair of outer cover members 51 and 52 which when pressed together form a hollow opening longitudinally disposed therebetween. Mounted in this opening are a pair of shafts 53 and 54 which, at one end, carry stationary supports 55 and 56 which together form the stationary jaw. The jaw is held together by suitable rivoted pins 104 or the like in holder 69. Also carried in the opening is a second pair of shafts 57 and 58 which carry at one end the supports 59 and 60 for the stationary portion of the actuating means and at the opposite end carry the supports 61 and 62 for the movable jaw. A holder 69 for the receiver portions of the fasteners is mounted between the stationary jaw supports and the holder 63 for the U-shaped staple portion of the fasteners is mounted between the movable jaw supports 61 and 62. A pusher 64 is mounted on a shaft 65 disposed in the center of the opening formed by the outer cover members. Mounted on top of the center shaft 65 is a movable member 66. The movable member is appropriately mounted through a screw 67 to the knob 68. Turning of the knob in one direction moves the pusher and the staple holder forwardly towards the receiver holder to set an appropriate gap between the staples and the receivers. Turning the knob in the opposite direction moves the pusher and staple holder away from the receiver holder to open the gap and allow tissue to be removed from between the staple holder and receiver holders.

Mounted between the supporting jaw members at the top thereof is a portion of means for holding tissue between the jaws and for locking the top of the jaws together to provide rigidity. This portion comprises a movable slotted member 70 having a pair of ears 71 and 72. The ears are disposed in slots 73 and 74 disposed in stationary supports 55 and 56. A compression spring 75 is mounted beneath the slotted member to allow the member to move up and down in the slots disposed in the stationary jaw members. Mounted on top of the outer cover members 51 and 52 and longitudinally thereto is the cooperating portion of the means for holding tissue and locking the jaws together for rigidity. This cooperating portion is a longitudinal movable member 76 that fits through an opening in the upper portion staple holder member 63. The longitudinally movable member is movable forwards and backwards with respect to the outer cover and is moved by the thumbs press 77. The movable member has a slot 78 at its free end and when moved forwardly, interlocks with the opening 58 in the movable slot member 70. A dog depends from the thumb press and fits into grooved member 100 mounted at the back and on top of the cover members. At the opposite end of the groove is a portion 101 that extends inwardly and engages in a slot in the knob 68. The portion 101 is guided in its movement by outer covers 51 and 52. Until the member is pushed as far forwardly as possible to remove the portion 101 from the slot in the knob, the knob cannot be rotated. Mounted from the staple holder are a pair of pawls 80 and 81 and mounted on the rigid shifts 53 and 54 is an anchor 82. The pawls are so disposed as to interlock with the anchor when the appropriate gap is set between the staple holding member 63 and the receiving holding member 69. The interlocking pawls and anchor provide added rigidity to the instrument and allow greater forces to be used when driving the staples through the tissue and into locking relationship with the receivers. At the opposite end of the instrument is mounted the trigger or actuating means 84. The actuating means comprises a movable trigger portion mounted between the supports 57 and 58 by a pin 87. A pivotal member 86 is encased by interlocking plastic handle halves 88 and 89 of the movable trigger. The pivotal member 86 includes an ear 90 which engages the shaft 65. The actuating means 84, members 61 and 62 and the shaft 65 are slideably mounted in slot 91 in the outer cover members 51 and 52. The stationary trigger portion comprises a pair of plastic handle halves 92 and 93. Mounted between the pivotal trigger and the stationary trigger is a pivotal interlocking member 85. This member is pivotally mounted between the stationary handles 92 and 93 and interlocks by engaging a pin 94 and spring 95 mounted in the movable portion of the trigger member. Mounted in the cover member 52 is a gauge to tell when the correct gap is attained between the receiver holder and the staple holder. The gauge comprises a marked member 105 that is linked to the screw member 67 and is mounted in position on the cover member 52 by a spring 106 and cover plate 107. Appropriate cover plates 108 for identification and to see the mark on the marked member are placed on the outside of the cover members.

Figure 6:
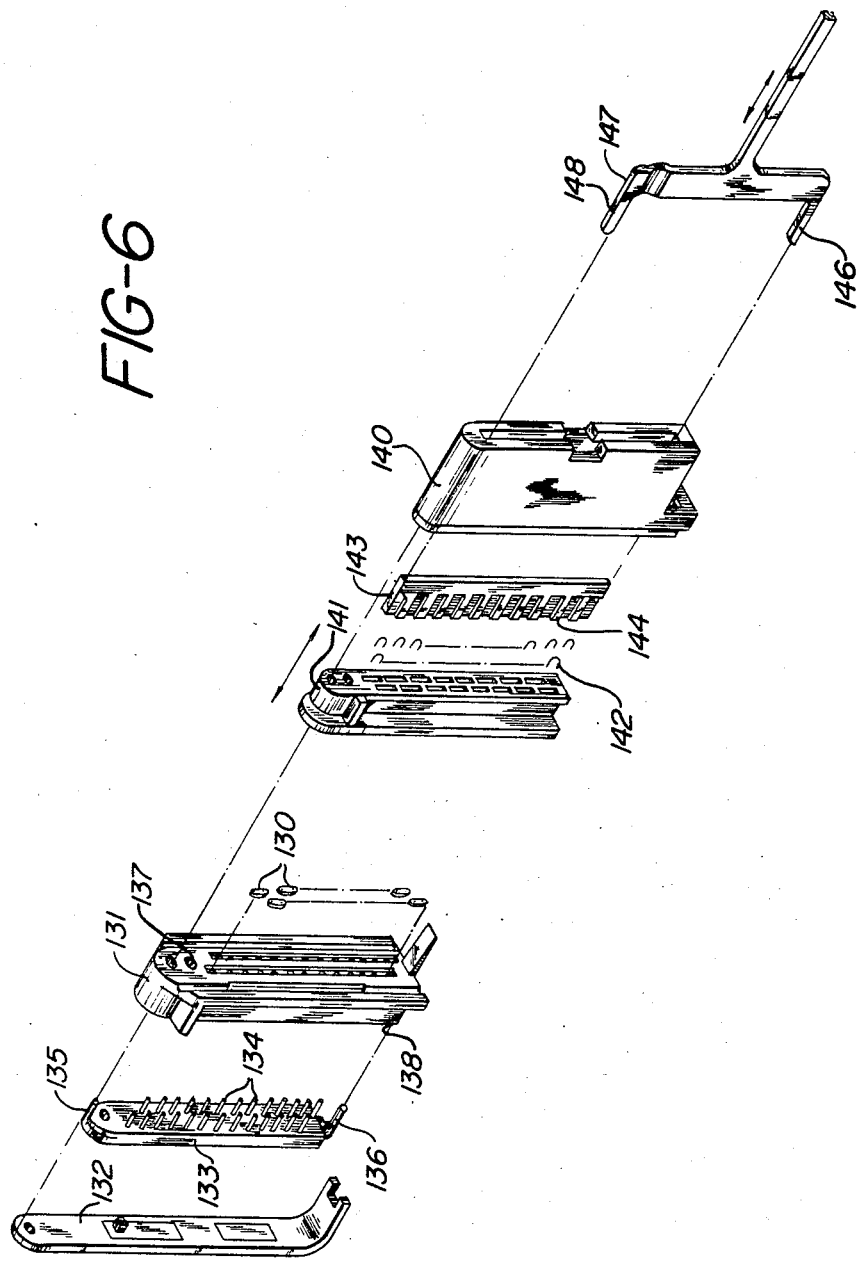
FIG. 6 is an exploded perspective view of the working parts of one embodiment of the jaws of an instrument of the present invention.

Referring to FIG. 6 there is shown an exploded perspective view of one embodiment of the working parts of the pair of jaws of instruments according to the present invention. Receivers, and in this instance they comprise members having a pair of openings disposed therein, are mounted in a stationary jaw and U-shaped staples with the legs of the U designed to enter the openings of the receivers are mounted in the movable jaw. The receivers 130 are mounted in a housing 131 mounted on the stationary jaw 132. The receivers are held in that housing by a movable member 133 which has pins 134 which frictionally engage the openings in the receivers. This holding member is movably mounted by virtue of an upper and a lower pin 135 and 136 respectively positioned in openings 137 and 138 in the receiver housing 131. The movable jaw 140 carries a housing 141 for holding the U-shaped staples 142. Mounted behind this housing is a first pusher means 143 having fingers 144 which engage the back end or the span of the U-shaped the staples. Second drive means 147 mounted at the rear of the jaw moves forwardly to drive the first drive means and push the staples out of the housing so that the legs of the staples engage the receiver. Along therewith pins 146 and 148 of the second drive means engage the pins 135 and 136 and push the pins through the opening in the housing into the receiving housing opening to push the pins 135 and 136 out of frictional engagement with the receivers thus allowing the receivers to interlock with the legs of the staple.

Figure 7:
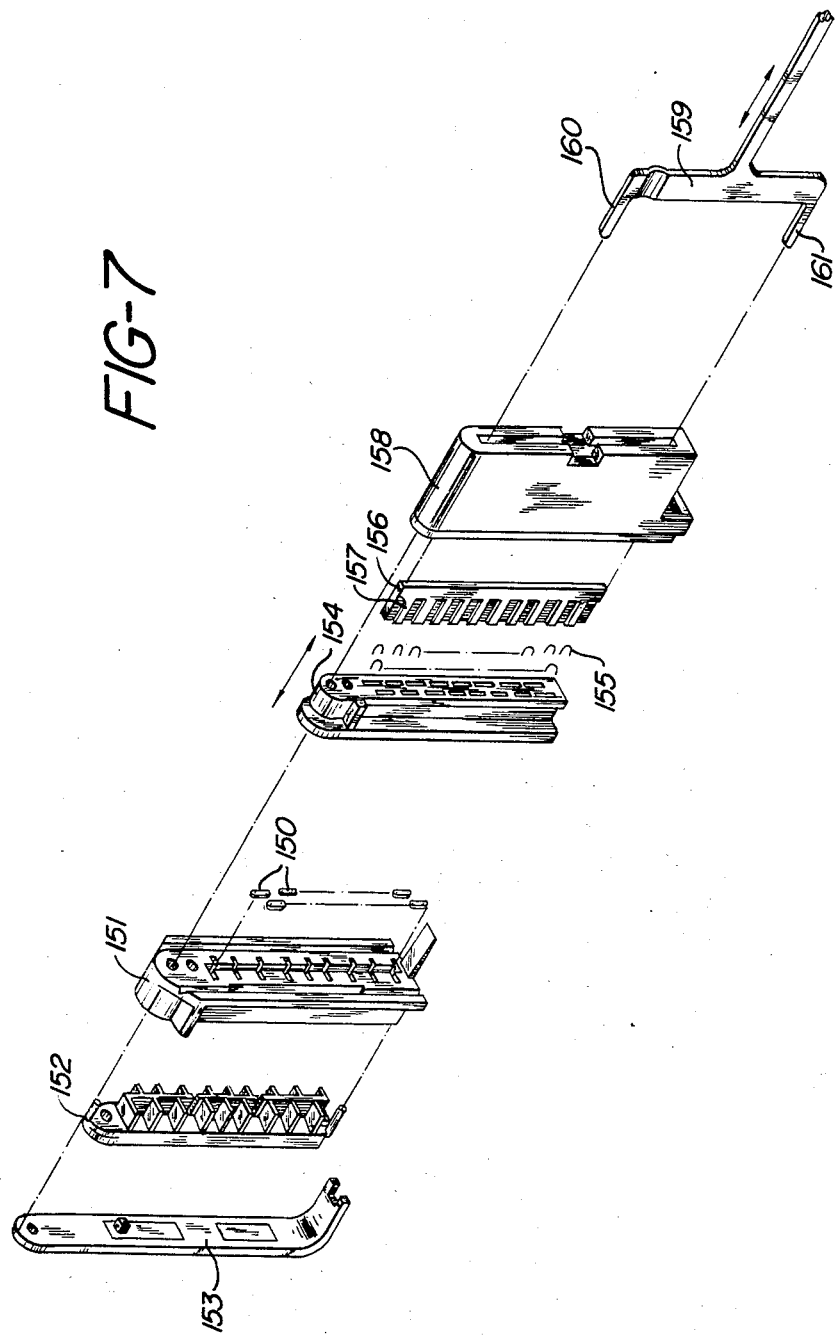
FIG. 7 is an exploded perspective view of the working parts of another embodiment of the jaws of an instrument of the present invention.

In FIG. 7 there is an exploded perspective view of another embodiment of the stationary and movable portions of the jaws for holding two-piece staples. In this embodiment the receivers 150 are held in a housing member 151 by a movable friction holding member 152 disposed within the housing. This friction member engages the outer periphery of the receivers to frictionally hold them within the housing. The receiver holding member and the friction holding member are mounted on the stationary jaw 153. A movable jaw 158 similar to that depicted in FIG. 6 comprises a staple housing member 154 for holding U-shaped staples 155. A first drive means 156 comprising individual fingers 157 which engage the staples to drive them. A second drive means 159 fits within the jaw to drive the first drive means and to also drive pins 160 and 161 at the same time that it drives the staple to cause the receiver friction holding member to move backward and disengage from the receivers allowing the receivers to be interlocked with the U-shaped staples.

An important part of the instruments of the present invention are the means disposed within the movable jaw for releasably holding individual staples in a manner to allow them to be appropriately driven through tissue to be joined and to have the legs of the staple align themselves in the openings of the receiver to interlock therewith.

Figure 8:
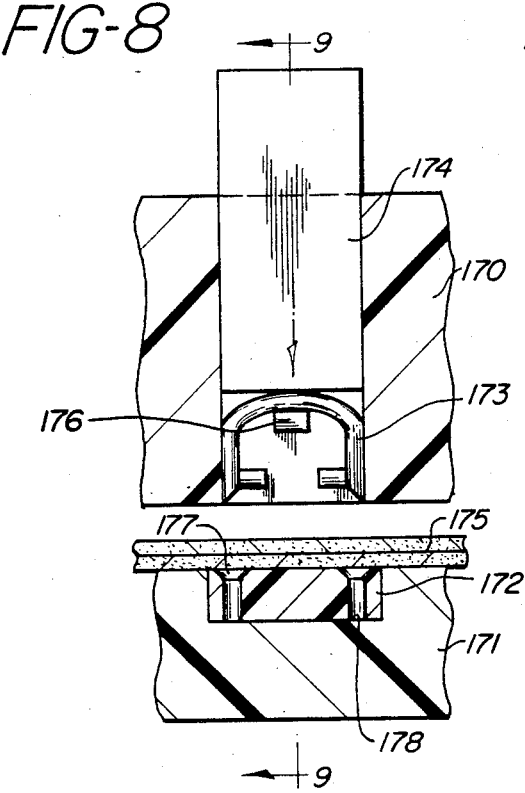
FIG. 8 is an enlarged cross-sectional view of a staple and receiver in the jaws of an instrument of the present invention.

FIG. 8 is an enlarged cross-sectional view of a staple holding portion of a movable jaw 170 and a receiver holding portion of a stationary jaw 171 showing a receiver 172 in place in the stationary jaw. A staple 173 is in place in the movable jaw and the individual finger driving means 174 for driving that staple is shown. The positioning of the jaws has been somewhat moved apart for the sake of clarity. In actual use, the tissue 175 is not rigid but is rather comformable and would tend to fill up the entire gap between the jaws.

Figure 9:
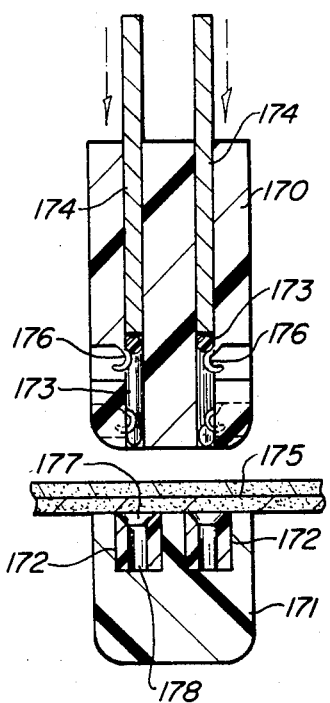
FIG. 9 is a cross-sectional view taken along line 9—9 of FIG. 8.

FIG. 9 is a cross-sectional view taken along Line 9—9 of FIG. 8. As may be seen each staple is held in position by movable flaps 176 disposed in the staple holding portion of the movable jaw.

Figure 10:
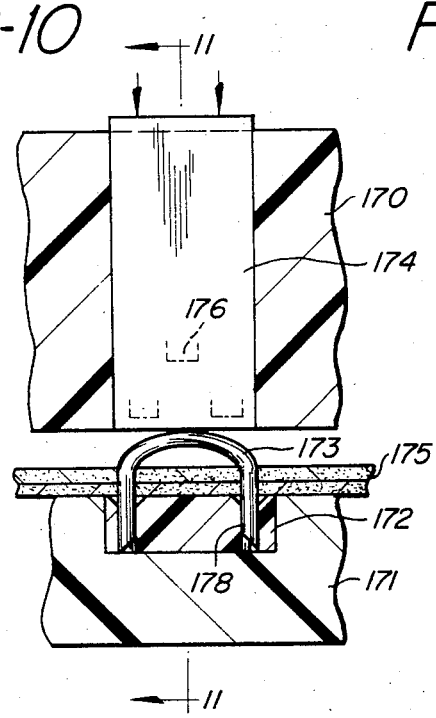
FIG. 10 is a cross-sectional view similar to FIG. 8 after the staple has been driven through tissue.
Figure 11:
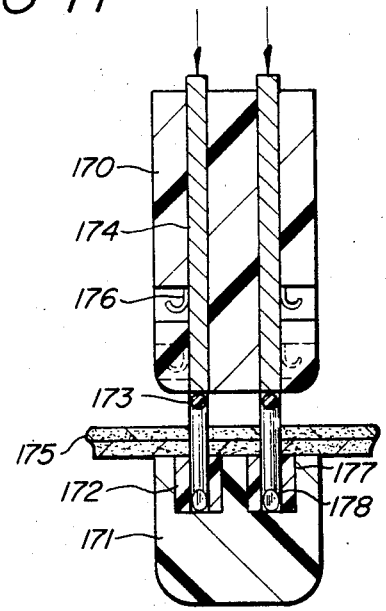
FIG. 11 is a cross-sectional view taken along line 11—11 of FIG. 10.
Figure 12:
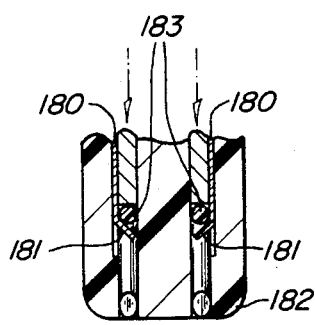
FIG. 12 is an enlarged cross-sectional view of a portion of a movable jaw showing one means for holding staples in jaw.

FIGS. 10 and 11 correspond to FIGS. 8 and 9; however, the staple has been driven through the tissue and the legs of the staple have been engaged by the receiver. As may be seen in these figures as the staple is driven down by the driver the flaps move out of the way and the expanded openings 177 in the receiver catch the legs of the staple and guide them into the frictional engaging portions 178 of the openings of the receiver.

Figure 13:
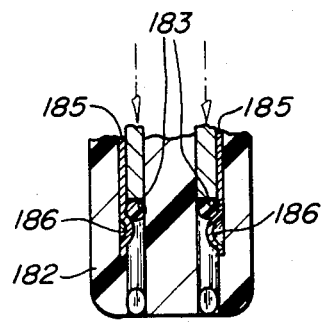
FIG. 13 is an enlarged cross-sectional view of a portion of a movable jaw showing another means for holding staples in the jaw.
Figure 14:
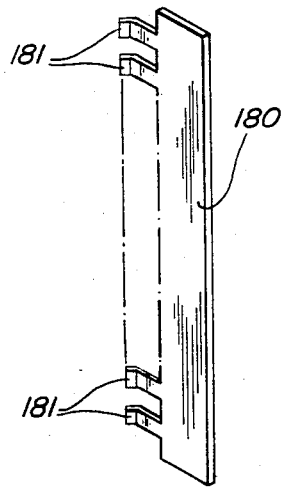
FIG. 14 is a perspective view of the means of FIG. 12.
Figure 15:
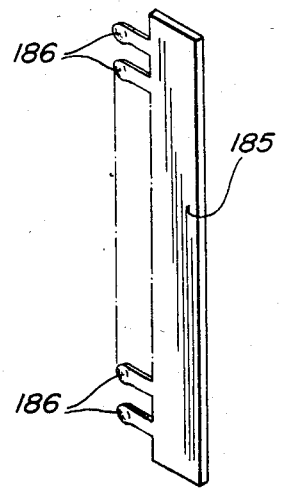
FIG. 15 is a perspective view of the means of FIG. 13.

FIGS. 12, 13, 14, and 15 show various modifications of means for holding the staples in the staple holding member. As may be seen in FIGS. 12 and 14 a member 180 having a plurality of deflectable fingers 181 may be disposed in the staple housing member 182 so that the bent end of each finger underlines the span between the legs of the U-shaped staple 183. As seen in FIGS. 13 and 15 the member 185 may carry a plurality of deflectable bubbles 186 which underline the span of the U-shaped staple leg. In both instances upon driving the staple the deflectable finger is moved out of the way or the bubble is deflected allowing the staple to be driven out of the staple holding member into the tissue.

Figure 16:
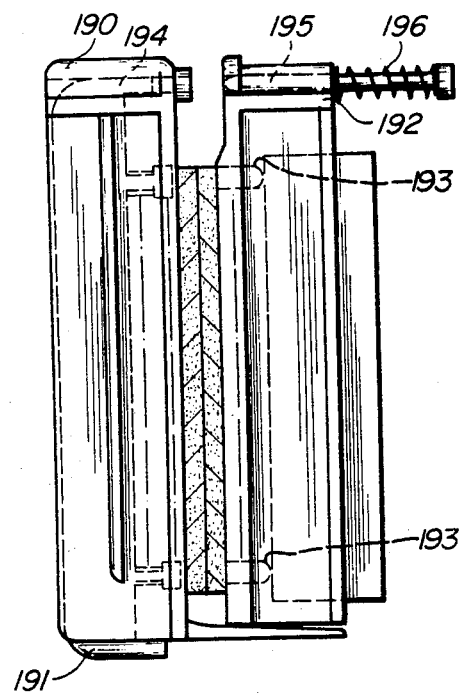
FIG. 16 is a cross-sectional view of the portion of the jaws of an instrument of the present invention just before the staples are caused to penetrate tissue.
Figure 17:
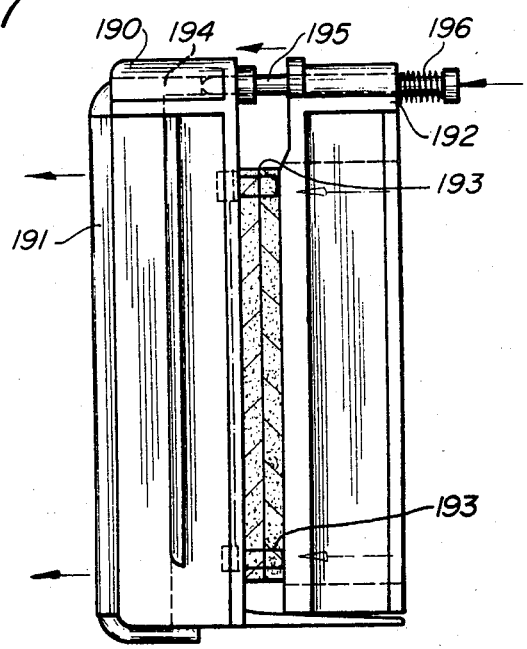
FIG. 17 is a cross-sectional view of the portions of the jaws depicted in FIG. 16 just after the staples have been caused to penetrate the tissue.

As described in conjunction with FIGS. 6 and 7, the receiver portion of the fastener is held in its housing member by friction means. The friction member may either engage the openings in the receiver or it may engage the outer portion or periphery of the receiver. However in any instance, once the legs of the staple have been forced into the receiver and interlock therewith the friction holding means of the receivers to be disposed from the instrument. FIGS. 16 and 17 show a preferred embodiment of moving the friction holding member out of the way. FIG. 16 depicts the jaws just before the staples have been driven through the tissue and FIG. 17 depicts the jaws just after the staples have been driven through the tissue. In FIG. 16 the stationary jaw 190 holds the movable receiver friction holding member 191. The movable jaw 192 holds the staples 193. The receiver friction holding member includes a pin portion 194 mounted in an opening in the stationary jaw. The movable jaw has a movable pin 195 mounted at its upper portion and in line with the pin on the receiver friction holding member. As may be seen in FIG. 17, the friction holding member 191 is moved out of the stationary jaw 190. As the staples from the movable jaw 192 are driven to penetrate the tissue and the legs of the staples engage with the openings of the receiver, the pin 195 mounted via a compression spring 196 at the top of the movable jaw is moved forwardly so that it enters the opening in the stationary jaw. As it enters the opening in the stationary jaw, it engages the pin extension of the friction holding member for the receivers and moves that friction holding member out of the way to allow the receivers to remain on the staple legs. Once the friction holding member has moved out of the way so that it has disengaged from the receivers, the jaws may be opened and the staples with the receivers interlocked with the legs will be in position joining the tissue.

As may be appreciated the instruments of the present invention may be made from metals, plastics, woods, similar materials or various combinations thereof. If it is desired to make the instruments disposable, then the more inexpensive materials should be used. In most instances, it is desirable to make the instruments disposable because they are relatively complicated intricate mechanisms which are difficult to resterilize.

The general operation of the instruments of the present invention is as follows. The tissues to be joined are placed between the stationary jaw and the movable jaw and are clamped in the space therebetween by moving the tissue locking member in the direction of the stationary jaw to interlock therewith. The tissue locking members aligns the jaws and once engaged allows the gap setting knob to be turned. On turning the gap setting knob the staple housing with the staples and the pusher and drive means is moved towards the stationary jaw. An appropriate gap, generally corresponding to the thickness of the tissues to be joined, is formed between the pair of jaws and is shown on the gauge. Thereafter, the interlock on the trigger mechanism is moved out of the way and the movable handle of the trigger mechanism actuated. This action forces the head of the pusher through the staple housing forcing the staples out of their holder through the tissue so that the legs pierce the tissue and engage the openings of the receivers held by the stationary jaw. Once the staple legs are engaged in the openings of the receivers, the friction holding means of the receivers is disengaged as well as the tissue locking means. After the joining operation has been completed, the gap between the jaws is opened by turning the gap control knob in the opposite direction.

It will be obvious to those skilled in the art that various modifications and changes may be made in the invention without departing from the spirit and scope thereof. The invention is not meant to be limited by that which is shown in the drawings and described in the specification. These changes and modifications are considered to fall within the scope of the present invention as defined by the appended claims.

What is claimed is:

1. In a surgical instrument for stitching tissue by means of two-piece fasteners, said fasteners comprising a substantially U-shaped staple member and a receiver to engage the legs of said U-shaped staple and lock therewith, said instrument having a pair of oppositely disposed jaws with the U-shaped staple members disposed in one jaw and the cooperating receivers disposed in said oposite jaw, said instrument including means for positioning the jaws with respect to each other while the tissue is therebetween to form an appropriate gap between the jaws and said instrument including means for driving the legs of the U-shaped member through the tissue to be joined and causing said legs to lock with the receiver in the opposite jaw, the improvement comprising friction means disposed in the jaw holding the receivers for holding said receivers in said jaw until the legs of the staple are locked with said receiver.

2. A surgical instrument according to claim 1 wherein the receiver has a pair of openings for accepting the legs of the U-shaped staple and the friction means for holding said receivers in the jaw comprises pins slideably disposed in said openings and frictionally engaged therewith.

3. A surgical instrument according to claim 1 wherein the friction means for holding the receivers in said jaws comprises a member frictionally engaging at least a portion of the outer periphery of each receiver to hold the receivers in place.

* * * * *